United States Patent [19]

Whitehouse et al.

[11] Patent Number: 4,981,469
[45] Date of Patent: Jan. 1, 1991

[54] SEPTUM ADAPTER ASSEMBLY AND EXTERNAL NEEDLE ADAPTER FITTING

[75] Inventors: Craig M. Whitehouse, Branford; Michael A. Sansone, Hamden, both of Conn.

[73] Assignee: DIJ Catheter Corp., Branford, Conn.

[21] Appl. No.: 182,968

[22] Filed: Apr. 18, 1988

[51] Int. Cl.⁵ .............................................. A61M 5/00
[52] U.S. Cl. .................................. 604/86; 604/283; 604/905
[58] Field of Search ................. 604/86, 201, 205, 280, 604/283, 167, 411, 414, 905; 141/329, 330; 222/83

[56] References Cited

U.S. PATENT DOCUMENTS

| | | |
|---|---|---|
| 4,116,066 | 9/1978 | Mehl et al. ............................ 604/414 |
| 4,346,703 | 8/1982 | Dennehey et al. .................... 604/905 |
| 4,369,781 | 1/1983 | Gilson et al. ......................... 604/905 |
| 4,511,359 | 4/1985 | Vaillancourt ......................... 604/411 |
| 4,559,043 | 12/1985 | Whitehouse et al. ................. 604/201 |
| 4,665,959 | 5/1987 | Takagi .................................. 604/905 |
| 4,752,292 | 6/1988 | Lopez et al. .......................... 604/283 |
| 4,786,281 | 11/1988 | Valentini et al. ..................... 604/905 |

FOREIGN PATENT DOCUMENTS 0157224  10/1985  European Pat. Off. ............ 604/283

Primary Examiner—John D. Yasko
Assistant Examiner—Anthony M. Gutowski
Attorney, Agent, or Firm—Levisohn, Lerner & Berger

[57] ABSTRACT

An assembly for connection to at least one medicant supply tube, includes (a) a septum assembly including a distal end cap having opposite first and second ends, an outer peripheral wall extending between the first and second ends and a bore extending therethrough from the first end to the second end; a septum cap including a puncture sealing section positioned over the first end and a securing section integrally formed with the puncture sealing section and positioned in fluid sealing contact with the peripheral wall adjacent the first end so as to secure the septum cap to the distal end cap; and a proximal connector connected with the distal end cap in covering relation to the septum cap, the proximal connector including a bore extending therethrough and a connection at one end thereof; and (b) an external adapter fitting having a septum piercing tube for piercing the puncture sealing section when the external adapter fitting is connected with the proximal connector, and a luer lock connection cooperating with the connection of the proximal connector for connecting the external adapter fitting to the proximal connector.

28 Claims, 4 Drawing Sheets

SEPTUM ADAPTER ASSEMBLY AND EXTERNAL NEEDLE ADAPTER FITTING

BACKGROUND OF THE INVENTION

This invention relates generally to an assembly that connects an adapter and needle to a tube for fluids such as a catheter or feed line for chemicals and the like.

In medical applications, it is often necessary to disconnect a drug delivery system connected to a catheter, for example, for the purpose of changing reservoirs or moving the patient. As a result, contaminants from the air or the surroundings may enter the open end of the tube that has been disconnected, adversely affecting the sterility of the line.

Related thereto, outpatient treatment for various illnesses frequently necessitates repeated injections of drugs by the patient at home. As a result, it is necessary to continuously remove and reinsert a catheter in the patient's body. Accordingly, hard teflon catheters have generally been used for such purpose. It would, however, be more desirable to utilize a soft catheter made of, for example, polyurethane, which could stay in the patient's body for an extended period of time on the order of a plurality of weeks or a month. Such soft catheters could be made much smaller, for example, having an outer diameter of 0.014 inch and an inner diameter of 0.004 inch, and would be more comfortable to the patient. However, in order to maintain such a catheter in the body for a long period of time during numerous reservoir changes, the internal catheter lumen must remain sterile in order to prevent contamination at the injection site.

In this regard, U.S. Pat. No. 4,659,043 discloses an assembly including a locking septum fitting which permits the disconnection and reconnection of a drug delivery system to an inserted catheter line while still maintaining sterility and leakproof characteristics within the catheter. In this regard, an assembly is disclosed therein which includes a septum disc that is compressed between a distal end cap and proximal connector connected to the distal end cap, so as to provide a self sealing, sterile, static barrier to a fluid being fed from a septum piercing tube, such as a needle, in an external adapter fitting connected to the proximal connector. However, the assembly of this Patent uses a seal that depends upon compression by the mating distal end cap and proximal connector. As a result, sealing occurs at the opposite faces of the septum disc which are contacted by respective portions of the distal end cap and proximal connector. In other words, the seal is not very efficient and because of the compression that is used to provide such seal, the seal may fail over a period of time, which could be disastrous to the patient. Also, because of such sealing arrangement, the component tolerances of the distal end cap and the proximal connector must be maintained very closely to insure proper sealing, thus greatly increasing the cost. Also, this arrangement limits the types of material that can be used for the septum itself. Specifically, some portion of the material must be sufficiently rigid to provide the proper support, while also allowing for repeated puncture.

However, the proximal connector and the distal end cap in this Patent are bonded together in order for the device to be operative. Thus, the proximal connector and the distal end cap must be held together in compression during the bonding operation. The bonded seam must also provide a static seal, as well as maintaining compression on the septum.

This Patent also discloses a taper sealing with a threaded lock connection between the external adapter fitting and the proximal connector.

An extension set and injection site is also sold by ICU Medical, Inc., 5200 Warner Avenue, Suite 108, Huntington Beach, Calif. 92649. With such device, the extension set includes a septum cap covering the end of an end cap. Such septum cap, however, is exposed at one end thereof, and as such has no secondary seal when connected to the external adapter fitting. In addition, an external adapter fitting which includes the needle extends over the septum cap during piercing thereof by the needle. However, an external snap-securing device is provided on the external adapter for securing the same to the extension set. This device complicates the assembly and makes it difficult to work with. This snap-securing device does not in itself provide a seal. The seal only takes place through the septum.

In the ICU device, there is a cowling that extends over the needle to provide a stickless needle.

OBJECTS AND SUMMARY OF THE INVENTION

Accordingly, it is an object of the present invention to provide a combination septum adapter assembly and external adapter fitting that overcomes the aforementioned disadvantages encountered in the prior art.

More particularly, it is an object of the present invention to provide such a combination that provides a double locking seal which can be connected or disconnected for a drug delivery tube or catheter end.

It is another object of the present invention to provide such a combination that provides a double seal with a septum cap and a luer lock.

It is still another object of the present invention to provide such a combination in which the septum cap is sealed along the annular side surface of the distal end cap to provide a larger and more reliable sealing area.

It is yet another object of the present invention to provide such a combination in which sealing does not occur by compression of the septum seal between the distal end cap and proximal connector.

It is further object of the present invention to provide such a combination that can be used to seal an open catheter end and to easily reattach a medicant supply line by means of a luer lock.

It is a still further object of the present invention to provide such a combination that is relatively easy and inexpensive to manufacture and use.

It is a yet further object of the present invention to provide such a combination in which the septum seal is more reliable.

It is another object of the present invention to provide such a combination in which component tolerances need not be as critical.

It is still another object of the present invention to provide such a combination in which the septum is bonded independently to the distal end cap so that the sealing is independent of the bonding between the distal end cap and the proximal connector.

It is yet another object of the present invention to provide such a combination in which assembly of the device is simplified since the compression load between the proximal connector and distal end cap need not be maintained while bonding such components together.

It is a further object of the present invention to provide such a combination in which the septum form allows more flexibility in the choice of materials, and particularly, the septum is no longer required to be of a rigid material.

It is a still further object of the present invention to provide such a combination in which the external adapter fitting has a cowling thereon.

In accordance with an aspect of the present invention, a septum assembly for connection to at least one medicant supply tube, includes a distal end cap having opposite first and second ends, an outer peripheral wall extending between the first and second ends and a bore extending therethrough from the first end to the second end; a septum cap including a puncture sealing section positioned over the first end and a securing section integrally formed with the puncture sealing section and positioned in fluid sealing contact with the peripheral wall adjacent the first end so as to secure the septum cap to the distal end cap; and a proximal connector connected with the distal end cap in covering relation to the septum cap, the proximal connector including a bore extending therethrough and connection means for connecting the proximal connector to a luer lock connection of an external adapter fitting having a septum piercing tube thereto in a fluid sealing manner.

In accordance with another aspect of the present invention, an assembly for connection to at least one medicant supply tube, includes (a) a septum assembly formed by a distal end cap having opposite first and second ends, an outer peripheral wall extending between the first and second ends and a bore extending therethrough from the first end to the second end; a septum cap including a puncture sealing section positioned over the first end and a securing section integrally formed with the puncture sealing section and positioned in fluid sealing contact with the peripheral wall adjacent the first end so as to secure the septum cap to the distal end cap; and a proximal connector connected with the distal end cap in covering relation to the septum cap, the proximal connector including a bore extending therethrough and connection means at one end thereof; and (b) an external adapter fitting having a septum piercing tube for piercing the puncture sealing section when the external adapter fitting is connected with the proximal connector, and luer lock connection means cooperating with the connection means of the proximal connector for connecting and locking the external adapter fitting to the proximal connector.

In accordance with still another aspect of the present invention, the external adapter fitting as defined in the previous paragraph further includes a cowling which extends over substantial portions of the distal end cap and proximal connector when the external adapter fitting is secured to the proximal connector.

In accordance with yet another aspect of the present invention, an external adapter fitting for connection to a septum assembly includes a main body; a septum piercing tube secured to the main body for piercing a puncture sealing section of the septum assembly when the external adapter fitting is connected with the septum assembly; tapered and threaded securing means formed with the main body and cooperating with connection means of the septum assembly for releasably connecting and locking the external adapter fitting to the septum assembly in a sealing manner; and cowling means connected to the threaded tapered securing means for covering the septum piercing tube.

The above and other objects, features and advantages of the present invention will become readily apparent from the following detailed description thereof which to be read in connection with the accompanying drawings.

DETAILED DESCRIPTION OF THE PREFERRED EMBODIMENTS

Figure 1:
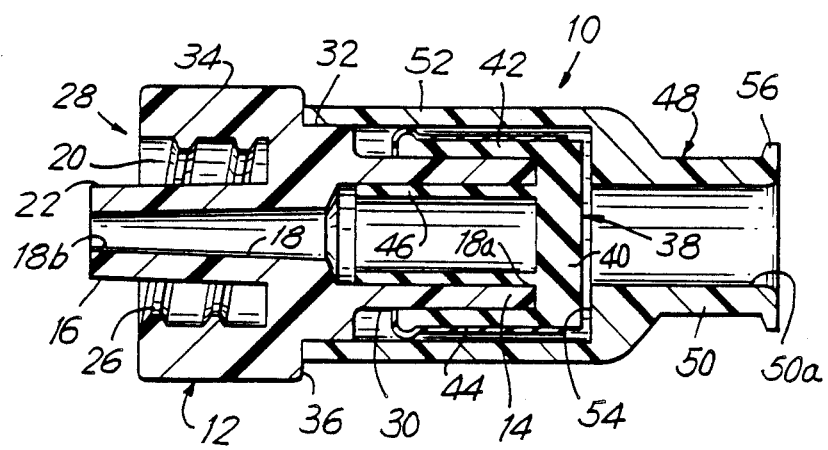
FIG. 1 is a cross-sectional view of a septum adapter assembly with a luer lock end according to a first embodiment of the present invention.

Referring to the drawings in detail, and initially to FIG. 1 thereof, a septum adapter assembly 10 according to one embodiment of the present invention includes a distal end cap 12 having first and second opposite ends 14 and 16, respectively, with a central bore 18 extending therethrough. Central bore 18 defines a fluid opening 18a at first end 14 and a fluid opening 18b at second end 16. Further, central bore 18 adjacent fluid opening 18a has a substantially constant diameter and starts tapering down substantially midway of distal end cap 12 toward fluid opening 18b at second end 16. An annular recess 20 is provided at second end 16 so as to define a male luer lock connection 28 formed by a male tapered fitting 22 and female thread 26 spaced apart by annular recess 20.

Distal end cap 12 is also formed with an external peripheral wall of varying diameter. Specifically, the external peripheral wall of distal end cap 12 includes a first outer wall 80 of constant diameter adjacent first end 14 which expands in a step-wise manner to a second outer wall 32 having a larger diameter, the latter expanding still further to the third and final outer wall 34 having a still larger diameter such that an annular step 36 is defined between second and third outer walls 32 and 34.

In accordance with an important aspect of the present invention, a septum cap 38 is provided in covering and sealing relation to first end 14 of distal end cap 12. Septum cap 38 is preferably made of an elastomer or any other suitable material and is formed with a disc-like section 40 that sits on the end surface of distal end cap 12 so as to cover surrounding central bore 18 at first end 14 thereof. Disc-like section 40 is puncturable and self-sealing, that is, after a needle punctures disc-like section 40 and extends into central bore 18, disc-like section 40 seals about the needle and reseals upon needle removal.

Septum cap 38 also includes an outer annular sealing section 42 that is integrally formed with and extends perpendicular from the outer peripheral edge of disc-like section 40 over the external surface of first outer wall section 30 in a tight-fitting manner. In other words, outer annular sealing section 42 is stretched over first outer wall 30. It is this tight fit which provides the fluid sealing of septum cap 38 on distal end cap 12. In order to absolutely ensure that outer annular sealing section 42 provides a fluid seal with first outer wall 30, a sealing band 44 can be provided therearound which is heat sealed so as to shrink and thereby apply pressure to outer annular sealing section 42 to press the same against first outer wall 30 so as to provide the aforementioned fluid seal and to lock septum cap 38 to distal end cap 12.

In addition, in order to provide a further fluid seal by septum cap 38, the latter is also formed with an inner annular sealing section 46 that is integrally formed with and extends perpendicular from disc-like section 40, spaced radially inwardly from outer annular sealing section 42. Inner annular sealing section 46 hugs the inner surface of first outer wall 30, within central bore 18, to provide an additional seal thereat. It will be appreciated that, although disc-like section 40 is on the outer edge at first end 14 of distal end cap 12, so as to provide still additional sealing thereat, disc-like section 40 of septum cap 38 can be spaced from first end 14 of distal end cap 12 since sealing occurs primarily by outer annular sealing section 42 and secondly by inner annular sealing section 46.

Septum assembly 10 further includes a proximal connector 48 which fits over septum cap 38 and first end 14 of distal end cap 12 to protect the same from contamination. Specifically, proximal connector 48 is bonded to distal end cap 12, and has a two-fold function. First, when the needle adapter fitting (FIG. 4) is attached thereto, it locks the needle adapter fitting to septum assembly 10, thereby preventing accidental disconnection. Secondly, an inner surface 50a of a first narrow annular section 50 of proximal connector 48, which provides a standard luer lock taper, provides a secondary seal to contamination with the needle adapter fitting, in addition to the septum seal provided about the needle.

Figure 7:
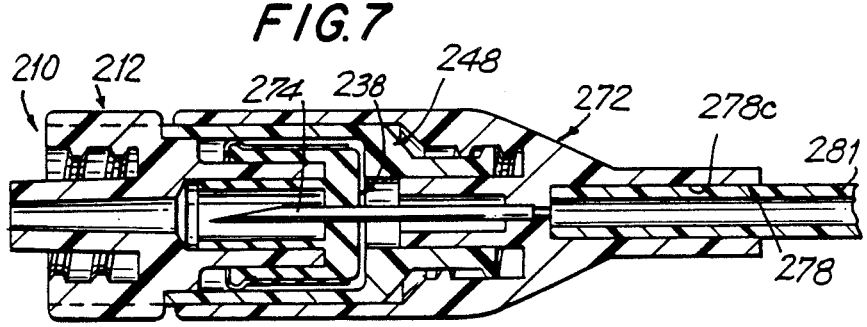
FIG. 7 is a cross-sectional view of a combination according to another embodiment of the present invention.

As shown, proximal connector 48 includes first narrow annular section 50 having an inner diameter generally smaller than that of disc-like section 40 of septum cap 38, and a wider annular section 52 connected to narrow annular section 50 and extendible over septum cap 38 and first end 14 of distal end cap 12 and permanently bonded and sealed to distal end cap 12. Thus, there is a sealed permanent bond between outer wall 32 and wider annular section 62. This bond serves two purposes. First, the bond creates a sterile seal so that contamination cannot reach the septum surface when the needle adapter fitting is in place, as shown in FIG. 7. Secondly, the bond provides the strength which holds the entire assembly 10 together. When the needle adapter fitting is locked by a luer lock thread, as described hereinafter, it is this bond which prevents distal end cap 12 from disconnecting from even a strong pulling force.

An annular shoulder 54 is defined at the connection of narrow annular section 50 with wider annular section 52. Specifically, wider annular section 52 fits snugly over second outer wall section 32 and abuts against annular step 36 so as to limit travel thereof. Preferably, annular shoulder 54 is spaced from the outer surface of disc-like section 40. Thus, it is clear that no compression of septum cap 38 occurs between distal end cap 12 and proximal connector 48. However, if desirable, annular shoulder 54 can abut the outer face of disc-like section 40 of septum cap 38, although such construction is unnecessary, as aforesaid, since sealing occurs by means of outer and inner annular sealing sections 42 and 46, respectively.

It will be appreciated that because a septum surface seal is not necessary, that is, because disc-like section 40 need not be sandwiched tightly between distal end cap 12 and proximal connector 48 to obtain a sealing effect, the tolerances of distal end cap 12, septum cap 38 and proximal connector 48 can be reduced. This is important since it is difficult to provide close tolerances on elastomer parts such as septum cap 38. Thus, the cost of the assembly can be greatly reduced by reducing tolerances to the point where annular shoulder 54 and disc-like section 40 of septum cap 38 are not required to be in contact. Accordingly, it is only necessary to provide the sealing effect at annular sealing section 42 of septum cap 38. By side sealing septum cap 38, a more reliable seal is formed and can be leak tested before bonding distal end cap 12 (with septum assembly 38 thereon) to proximal connector 48.

In addition, the free end of proximal connector 48 includes an outwardly directed circumferential flange 56 for mating with a luer lock connector of an external needle adapter fitting, to be described hereinafter.

Figure 2:
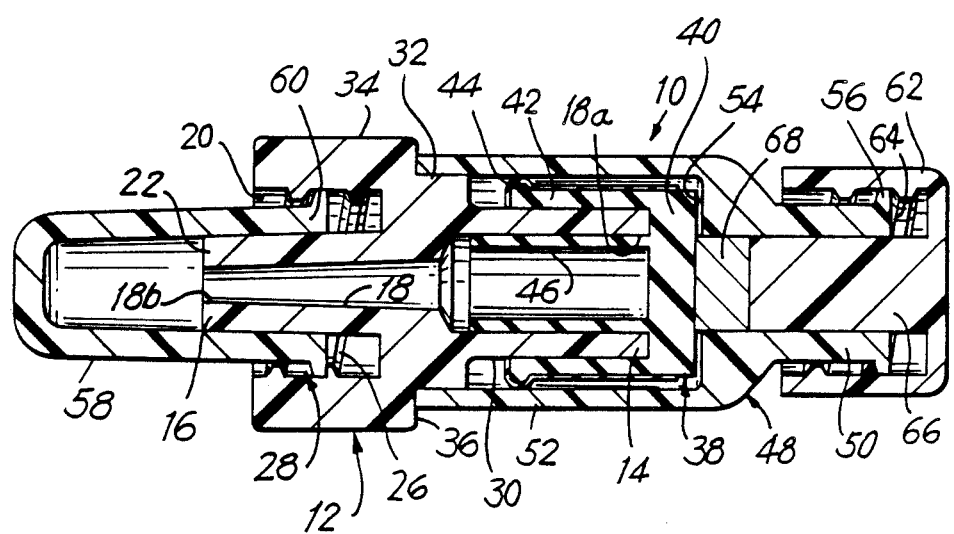
FIG. 2 is a cross-sectional view of the assembly of FIG. 1, with end caps secured thereto.

As shown in FIG. 2, when septum assembly 10 is not in use, a female luer lock protective cap 58 having an outwardly directed circumferential flange 60 at the open end thereof can be screw-threadedly received with luer lock connection 28 of distal end cap 12 to prevent contaminants from entering through central bore 18. In like manner, a protective cap 62 having internal screw threads 64 which define a male luer lock connection can be screw-threadedly received with circumferential flange 56 of proximal connector 48. As is well-known in the art, due to a mating of tapered surfaces, luer lock connections provide a fluid seal. As a result, protective caps 58 and 62, along with septum cap 38 provide an absolute fluid seal for the internal bore 18 of septum assembly 10. In addition, protective cap 62 includes a central post 66 as part of the luer lock, which extends through the central bore of narrow annular section 50 when protective cap 62 is connected with proximal connector 48. A sterility swab 68 can be provided at the free end of central post 66 so that it contacts the outer surface of disc-like section 40 of septum cap 38 to provide a sterile surface for the same when not in use. Of course, in using septum assembly 10, protective caps 58 and 62 are removed, along with sterility swab 68.

Figure 3:
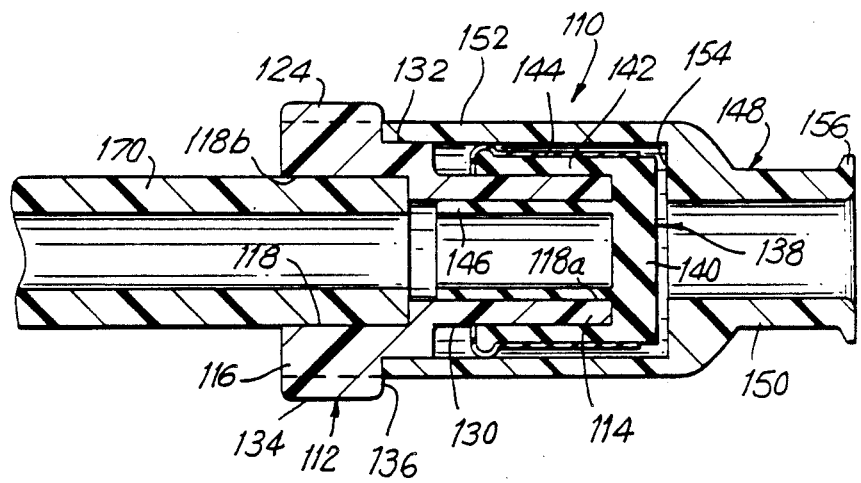
FIG. 3 is a cross-sectional view of a septum adapter assembly with a tube end according to another embodiment of the present invention.

Referring now to FIG. 3, a septum assembly 110 according to another embodiment of the present invention, will now be described, in which elements similar to those described above with respect to the embodiment of FIGS. 1 and 2 are identified by the same reference numerals augmented by 100, and a detailed description thereof is omitted herein for the sake of brevity.

Specifically, with septum assembly 110, distal end cap 112 is formed without male luer lock connection 28. As a result, the distal end cap has a smooth inner surface of a constant diameter which is adapted to receive the end of a flexible tube 170. In all other respects, septum assembly 110 is identical to septum assembly 10.

Figure 4:
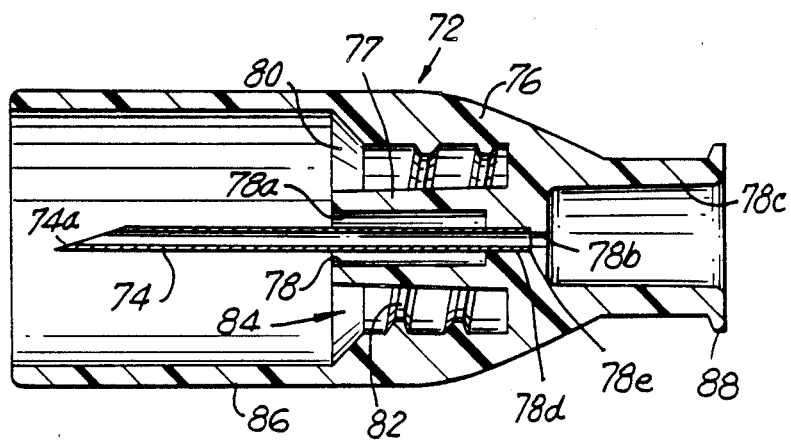
FIG. 4 is a cross sectional view of an external needle adapter fitting having a septum piercing needle according to the present invention for connection with the assemblies of FIGS. 1-3.

Referring now to FIG. 4, an external needle adapter fitting 72 having a septum piercing tube such as a needle 74 secured thereto may be provided. Specifically, external adapter fitting 72 includes a main body 76 with a central bore 78 therethrough having a distal bore section 78a, central bore sections 78d and 78b contiguous therewith and having smaller diameters than distal bore section 78a and a large diameter bore section 78c contiguous with central bore section 78b. Central bore section 78b has a smaller diameter than the outer diameter of needle 74 and central bore section 78d has the same diameter as the outer diameter of needle 74. Accordingly, needle 74 fits through distal bore section 78a and is snugly fit into central bore section 78d, and abuts a shoulder 78e formed between central bore sections 78d and 78b. Needle 74 is bonded to main body 76 by filling bore 78a with glue. Bore 78b prevents the glue from wicking into the needle bore. Alternatively, needle 74 may extend into large diameter bore section 78c, instead of abutting against shoulder 78e.

With such arrangement as shown in FIG. 4, the beveled or sharp end 74a of needle 74 extends outwardly from first bore section 78a. An annular recess 80 is provided so as to define a male luer lock connection 84 formed by a male tapered fitting 77 and female thread 82 spaced apart by annular recess 80. In addition, an annular cowling 86 is connected to the end of male luer lock connection 84 of external adapter fitting 72 in surrounding relation to the free end of needle 74. Cowling 86 extends beyond needle tip 74a.

In addition, such other end of external adapter fitting 72 includes a female luer lock taper 78c and flange 88 which is adapted to mate with a male luer lock threaded connection.

Figure 5:
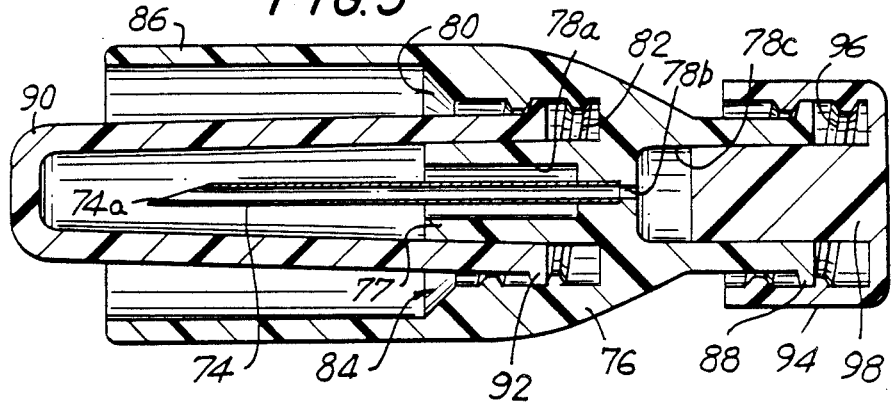
FIG. 5 is a cross-sectional view of the external needle adapter fitting of FIG. 4 with end caps secured thereto.

As shown in FIG. 5, when not in use, a female luer lock protective cap 90, which ia similar to protective cap 58, has a female luer lock taper at the open end 92 thereof which forms a seal with male luer lock 84 when connected. In addition, another male luer lock protective cap 94 which is similar to protectiVe cap 62 is proVided and includes a male luer lock formed by internal screw threads 96 and a tapered central post 98 that fits within proximal tapered bore section 78c, such that protective cap 94 can be screw-threadedly received at the opposite end of external adapter fitting 72. In this manner, the internal bore of external adapted fitting 72 is protected from contamination during non-use.

An assembly according to the first embodiment of the present invention is formed with septum assembly 10 of FIGS. 1 and 2 and external adapter fitting 72 of FIGS. 4 and 5. Specifically, protective caps 58, 62, 90 and 94 are removed, and then external adapter fitting 72 is connected in a fluid sealing manner with septum assembly 10. In this regard, outwardly directed circumferential flange 56 of proximal connector 48 is screw-threadedly received with luer lock connection 84 so as to provide a fluid seal thereat. During such assembly, needle 74 punctures and penetrates through disc-like section 40 of septum cap 38, whereby septum cap 38 seals around needle 74. Accordingly, a double seal is provided, that is, septum cap 38 about needle 74 and by means of luer lock connection 84. As a result, the assembly of FIG. 6, when distal end 12 is connected to a tube or catheter female luer fitting, can be used to connect and disconnect the drug delivery tube or inserted catheter without compromising sterility. In addition, when so connected, cowling 86 covers proximal connector 48.

A variant of the assembly according to another embodiment of the present invention is shown in FIG. 7 in which elements corresponding to those described above in respect to the assembly of FIG. 6 are identified by the same reference numerals, augmented by 200, and a detailed description thereof will be omitted herein for the sake of brevity. Specifically, as shown therein, the assembly of FIG. 7 differs from that of FIG. 6 by eliminating circumferential flange 88 on external adapter fitting 272. Accordingly, a luer lock connection cannot be provided at such end. Instead, a flexible tube 281 is merely force fit and bonded within proximal bore section 278c of external adapter fitting 272.

Figure 6:
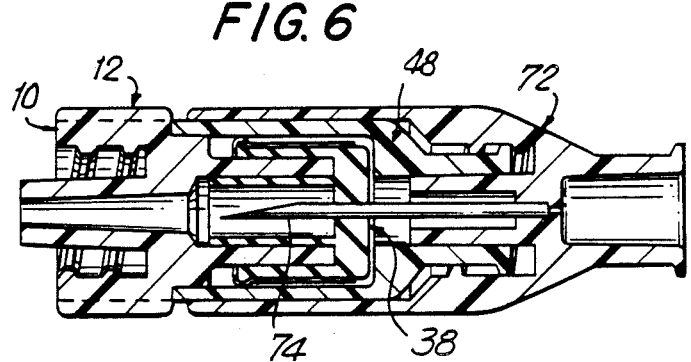
FIG. 6 is a cross-sectional view of the combination of the septum assembly FIG. 1 and external needle adapter fitting of FIG. 4 connected together.
Figure 8:
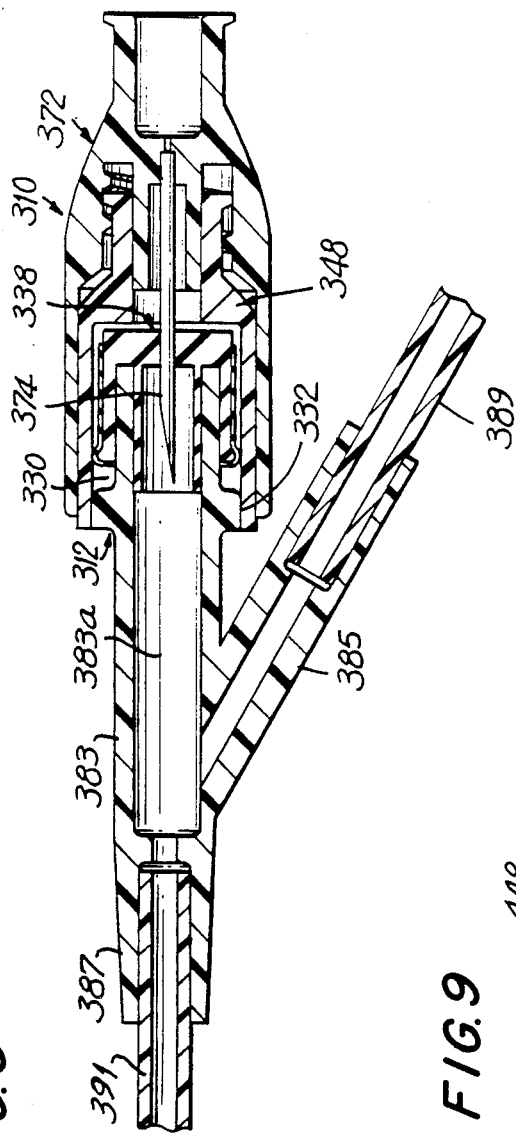
FIG. 8 is a cross-sectional view of a combination according to another embodiment of the present invention.

Another variation of the assembly of FIG. 6 is shown in FIG. 8, in which elements that are similar to those in the assembly of FIG. 6 are identified by the same reference numerals augmented by 300, and a detailed description thereof will be omitted herein for the sake of brevity. The assembly of FIG. 8 differs from the assembly of FIG. 6 as to distal end cap 312 which eliminates male luer lock connection 28. Rather, from second outer wall section 332, the remainder of distal end 312 is formed by a Y-site connector having a first tube leg 383 connected with a second tube leg 385 which extends at an acute angle therefrom. First tube leg 383 is also connected to a common leg 387, second tube leg 385 and common tube leg 387 having central bores which receive flexible tubes 389 and 391, respectively, which are bonded therein. In this manner, an auxiliary medicant can be supplied through tube 389 and second tube leg 385 to mix with the medicant supplied by needle 374.

It is clear that septum adapter assembly 310 could just as easily be attached to the second angled tube leg 385 and not the first in line tube leg 383. The bore 383a in first tube leg 383 can also be reduced in diameter to decrease dead volume.

Figure 9:
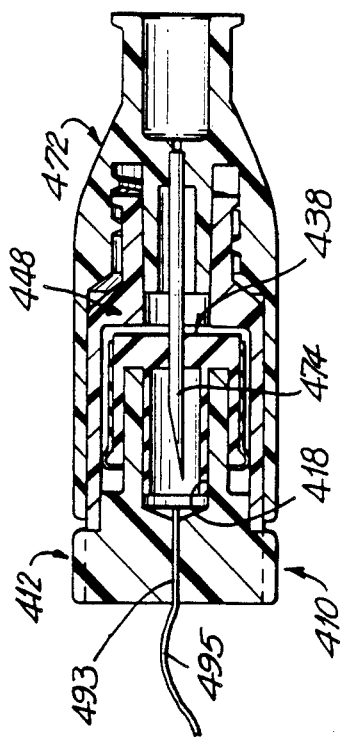
FIG. 9 is a cross-sectional view of a combination according to another embodiment of the present invention.

Still another variation according to the present invention is shown in FIG. 9 in which elements similar to those described above with respect to the embodiment of FIG. 6 are identified by the same reference numerals augmented by 400 and a detailed description thereof will be omitted herein for the sake of brevity. Specifically, in place of male luer lock connection 28, the distal end cap is made substantially solid with a small diameter bore 493 through which a catheter 495 extends into fluid communication with bore 418 of distal end cap 412 for supply a medicant directly to the patient. Catheter 495 may be bonded within bore 493.

Having described specific preferred embodiments of the invention with reference to the accompanying drawings, it will be appreciated that the present invention is not limited to those precise embodiments, and that various changes and modifications can be effected therein by one of ordinary skill in the art without departing from the spirit or scope of the invention as defined by the appended claims.

What is claimed is:

1. A septum assembly for connection to at least one medicant supply tube, said assembly comprising:
   a distal end cap having opposite first and second ends, an outer peripheral wall extending between said first and second ends and a bore extending therethrough from said first end to said second end;
   a septum cap including a puncture sealing section positioned over said first end and a securing section integrally formed with said puncture sealing section and positioned in fluid sealing contact with said peripheral wall adjacent said first end so as to secure said septum cap to said distal end cap, said peripheral wall of said distal end cap including a first outer wall adjacent said first end and a second outer wall having a larger diameter than said first outer wall and connected thereto by an annular step;

a proximal connector connected with the distal end cap in covering relation to said septum cap, said proximal connector including a bore extending therethrough and connection means for connecting said proximal connector to a luer lock connection of an external adapter fitting having a septum piercing tube in a fluid sealing manner; said proximal connector being fixedly connected to said second outer wall and spaced apart from said first outer wall; and said peripheral wall of said distal end cap further including a third outer wall adjacent said second end, said third outer wall connected to said second outer wall by a second annular step, said third outer wall having a diameter larger than said second annular wall, and said proximal connector having a free end that abuts against said second annular step when said proximal connector is connected to said second outer wall.

2. A septum assembly according to claim 1; wherein said securing section of said septum cap includes an outer annular securing wall secured to said puncture sealing section and positioned in fluid sealing contact with the outer surface of said peripheral wall adjacent said first end and an inner annular securing wall secured to said puncture sealing section radially inwardly of said outer annular securing wall and positioned in fluid sealing contact with the inner surface of said peripheral wall adjacent said first end.

3. A septum assembly according to claim 2; wherein said puncture sealing section includes an annular disc-like sealing member connected to said outer and inner annular sealing walls.

4. A septum assembly according to claim 1; further including a sealing band secured tightly about said securing section so as to force said securing section into sealing contact radially inwardly with said peripheral wall adjacent said first end.

5. A septum assembly according to claim 1; wherein said proximal connector is spaced from said septum cap.

6. A septum assembly according to claim 1; wherein said distal end cap includes a male luer lock fitting at said second end.

7. A septum assembly according to claim 1; wherein said distal end cap includes an annular recess at said second end thereof which defines a male tapered fitting formed by a male tapered portion and a f%,male outer thread.

8. A septum assembly according to claim 1; wherein said distal end cap includes Y-connection means at the second end thereof for connecting two tubes thereto.

9. A septum assembly according to claim 1; wherein said distal end cap includes tubing connection means at said second end thereof for connecting a tube thereto.

10. A septum assembly according to claim 9; wherein said bore through the second end of said distal end cap has a greatly reduced diameter at said second end thereof to define said tube connection means and to thereby receive a catheter tube therein.

11. A septum assembly according to claim 1; further including a distal end cap covering means for covering and sealing the bore at the second end of said distal end cap during non-use of said septum assembly and proximal end covering means for engaging with the connection means during non-use of said septum assembly to cover and seal the bore thereat.

12. A septum assembly according to claim 1; wherein said connection means includes a female tapered locking connection.

13. An assembly for connection to at least one medicant supply tube, said assembly comprising:
(a) a septum assembly including:
(i) a distal end cap having opposite first and second ends, an outer peripheral wall extending between said first and second ends and a bore extending therethrough from said first end to said second end, said peripheral wall of said distal end cap including a first outer wall adjacent said first end and a second outer wall having a larger diameter than said first outer wall and connected thereto by an annular step;
(ii) a septum cap including a puncture sealing section positioned over said first end and a securing section integrally formed with said puncture sealing section and positioned in fluid sealing contact with said peripheral wall adjacent said first end so as to secure said septum cap to said distal end cap; and
(iii) a proximal connector connected to the distal end cap in covering relation to said septum cap, said proximal connector including a bore extending therethrough and connection means at one end thereof, said proximal connector being fixedly connected to said second outer wall and spaced from said first outer wall, said peripheral wall of said distal end cap further including a third outer wall adjacent said second end, said third outer wall connected to said second outer wall by a second annular step and having a diameter larger than said second annular wall, said proximal connector having a free end that abuts against said second annular step when said proximal connector is fixedly connected to said second outer wall; and
(b) an external adapter fitting having a septum piercing tube for piercing said puncture sealing section when said external adapter fitting is connected to said proximal connector, and luer lock connection means cooperating with said connection means of said proximal connector for releasable connecting the external adapter fitting to said proximal connector.

14. An assembly according to claim 13; wherein said securing section of said septum cap includes an outer annular securing wall secured to said puncture sealing section and positioned in fluid sealing contact with the outer surface of said peripheral wall adjacent said first end and an inner annular securing wall secured to said puncture sealing section radially inwardly of said outer annular securing wall and positioned in fluid sealing contact with the inner surface of said peripheral wall adjacent said first end.

15. An assembly according to claim 14: wherein said puncture sealing section includes an annular disc-like sealing member connected to said outer and inner annular sealing walls.

16. An assembly according to claim 13; further including a sealing band secured tightly about said securing section so as to force said securing section into sealing contact with said peripheral wall adjacent said first end.

17. An assembly according to claim 13; wherein said proximal connector is spaced from said septum cap.

18. An assembly according to claim 13; wherein said distal end cap includes a male luer lock fitting at said second end.

19. An assembly according to claim 18; wherein said distal end cap includes an annular recess at said second end thereof which defines a male tapered fitting formed by a male tapered portion and an outer female thread.

20. An assembly according to claim 13; wherein said distal end cap includes Y-connection means at the second end thereof for connecting two tubes thereto.

21. An assembly according to claim 13; wherein said distal end cap includes tube connection means at said second end thereof for connecting a tube thereto.

22. An assembly according to claim 21; wherein said bore through the second end of said distal end cap has a greatly reduced diameter at said second end thereof to define said tube connection means and to thereby receive a catheter tube therein.

23. An assembly according to claim 13; further including distal end cap covering means for covering and sealing the bore at the second end of said distal end cap during non-use of said assembly and proximal end covering means for engaging with the connection means during non-use of said assembly to cover and seal the bore thereat.

24. An assembly according to claim 13; wherein said connection means includes a female tapered locking connection.

25. An assembly according to claim 13; wherein said external adapter fitting includes a main body with securing means for securing said septum piercing tube thereto such that said septum piercing tube extends away from said main body, and cowling means for covering said septum piercing tube.

26. An assembly according to claim 25; wherein said external adapter fitting has a central bore therethrough, said central bore including a reduced diameter section as said securing means for receiving said septum piercing tube therein in a fixed manner.

27. An assembly according to claim 26; wherein said external adapter fitting includes an annular recess adjacent said septum piercing tube which defines an inner male tapered fitting in surrounding relation to said septum piercing tube and a outer female thread.

28. An assembly according to claim 27; wherein said external adapter fitting includes a female tapered locking connection at an end thereof opposite said male tapered fitting for connection to another male tapered fitting.

* * * * *